US00PP18210P2

(12) United States Plant Patent
Miyazaki

(10) Patent No.: US PP18,210 P2
(45) Date of Patent: Nov. 13, 2007

(54) ***MECARDONIA* PLANT NAMED 'SUNMECAREKI'**

(50) Latin Name: ***Mecardonia* sp.**
Varietal Denomination: Sunmecareki

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/444,250

(22) Filed: May 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Mecardonia* plant named 'Sunmecareki', characterized by its compact, decumbent and mounded plant habit; freely branching habit; early and freely flowering habit; long flowering period; and small bright yellow-colored flowers.

1 Drawing Sheet

Botanical designation: *Mecardonia* sp.
Cultivar denomination: 'Sunmecareki'.

BACKGROUND OF THE INVENTION

The present invention relates to a new and distinct cultivar of *Mecardonia* plant, botanically known as *Mecardonia* sp., and hereinafter referred to by the name 'Sunmecareki'.

The new *Mecardonia* is a product of a planned breeding program conducted by the Inventor in Yamanashi, Japan. The objective of the breeding program is to create new compact *Mecardonia* cultivars with desirable flower and plant qualities and attractive foliage and flower coloration.

The new *Mecardonia* originated from a cross-pollination made by the Inventor in Yamanashi, Japan in June, 1995 of two unnamed proprietary seedling selections of *Mecardonia* sp., not patented. The cultivar Sunmecareki was discovered and selected by the Inventor as a flowering plant from within the progeny of the stated cross-pollination in a controlled environment in Yamanashi, Japan.

Asexual reproduction of the new *Mecardonia* by terminal cuttings in a controlled environment in Shiga, Japan since October, 2000, has shown that the unique features of this new *Mecardonia* are stable and reproduced true to type in successive generations.

SUMMARY OF THE INVENTION

The cultivar Sunmecareki has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunmecareki'. These characteristics in combination distinguish 'Sunmecareki' as a new and distinct cultivar of *Mecardonia:*

1. Compact, decumbent and mounded plant habit.
2. Freely branching habit.
3. Early and freely flowering habit.

4. Long flowering period.
5. Small bright yellow-colored flowers.

In side-by-side comparisons conducted in Shiga, Japan, plants of the new *Mecardonia* differed from plants of the female parent selection in the following characteristics:

1. Plants of the new *Mecardonia* had shorter internodes than plants of the female parent selection.
2. Plants of the new *Mecardonia* were more freely branching than plants of the female parent selection.

In side-by-side comparisons conducted in Shiga, Japan, plants of the new *Mecardonia* differed from plants of the male parent selection in the following characteristics:

1. Plants of the new *Mecardonia* were larger than plants of the male parent selection.
2. Plants of the new *Mecardonia* had larger flowers than plants of the male parent selection.

Plants of the new *Mecardonia* can be compared to plants of the *Mecardonia* cultivar USMECA67, disclosed in U.S. Plant Pat. No. 15,777. In side-by-side comparisons conducted in Shiga, Japan, plants of the new *Mecardonia* differed from plants of the cultivar USMECA67 in the following characteristics:

1. Plants of the new *Mecardonia* were more compact than plants of the cultivar USMECA67.
2. Plants of the new *Mecardonia* were more freely branching than plants of the cultivar USMECA67.
3. Plants of the new *Mecardonia* had ovate-shaped leaves whereas plants of the cultivar USMECA67 had elliptic-shaped leaves.
4. Plants of the new *Mecardonia* flowered earlier and more freely than plants of the cultivar USMECA67.

BRIEF DESCRIPTION OF THE PHOTOGRAPHS

The accompanying photographs illustrate the overall appearance of the new *Mecardonia.* These photographs show the colors as true as it is reasonably possible to obtain in colored reproductions of this type. Colors in the photographs may differ slightly from the color values cited in the detailed botanical description which accurately describe the colors of the new *Mecardonia*.

The photograph at the top of the first sheet comprises a side perspective view of a typical flowering plant of 'Sunmecareki' grown in a container.

The photograph on the second sheet is a close-up view of typical flowers of 'Sunmecareki'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Shiga, Japan during the spring in 15-cm containers in a polyethylene-covered greenhouse and under conditions and practices which approximate those generally used in commercial *Mecardonia* production. During the production of the plants, day temperatures averaged 18° C. and night temperatures averaged 14° C. Measurements and numerical values represent averages for typical four to five-month old flowering plants.

Botanical classification: *Mecardonia* sp. cultivar Sunmecareki.

Parentage:

*Female, or seed, parent.*—Unnamed proprietary seedling selection of *Mecardonia* sp., not patented.

*Male, or pollen, parent.*—Unnamed proprietary seedling selection of *Mecardonia* sp., not patented.

Propagation:

*Type.*—Vegetative cuttings.

*Time to initiate roots.*—About one week at 18° C. to 22° C.

*Time to produce a rooted cutting.*—About three weeks at 20° C. to 25° C.

*Root description.*—Fine, fibrous, white in color.

*Rooting habit.*—Freely branching.

Plant description:

*Plant form/growth habit.*—Compact, decumbent and mounding plant habit. Strong and vigorous growth habit.

*Plant height.*—About 4.6 cm.

*Plant diameter or spread.*—About 24.8 cm.

*Lateral branches.*—Quantity per plant: Freely branching habit with about 30 lateral branches developing per plant. Length: About 5.7 cm. Diameter: About 1.1 mm. Internode length: About 1.1 cm. Texture: Pubescent. Color: 145A.

Foliage description:

*Arrangement.*—Opposite, simple.

*Length.*—About 1.6 cm.

*Width.*—About 1 cm.

*Shape.*—Ovate.

*Apex.*—Acute.

*Base.*—Rounded.

*Margin.*—Serrate.

*Texture, upper and lower surfaces.*—Smooth, glabrous.

*Venation pattern.*—Pinnate; reticulate.

*Color.*—Developing and fully expanded foliage, upper surface: 144A; venation, similar to lamina. Developing and fully expanded foliage, lower surface: 144B; venation, similar to lamina.

*Petiole length.*—About 1.5 mm.

*Petiole diameter.*—About 0.7 mm.

*Petiole texture, upper and lower surfaces.*—Smooth, glabrous.

*Petiole color, upper and lower surfaces.*—144B.

Flower description:

*Flower arrangement and habit.*—Solitary axially flowers that face mostly upward or outward. Freely flowering habit with about 143 flowers per plant at one time.

*Natural flowering season.*—Long flowering period; spring until late autumn in Japan; flowering continuous during this period.

*Flower longevity on the plant.*—About five days. Flowers not persistent.

*Fragrance.*—Pleasant.

*Flower diameter.*—About 1.7 cm.

*Flower depth (height).*—About 8 mm.

*Throat diameter.*—About 1 mm.

*Tube diameter.*—About 1.8 mm.

*Flower buds.*—Length: About 9 mm. Diameter: About 5 mm. Shape: Ellipsoidal. Color: 9B.

*Corolla.*—Arrangement: Single whorl of four fused petals. Petal length, all petals: About 6.4 mm. Petal width, upper petal: About 8.8 mm. Petal width, lateral and lower petals: About 7 mm. Petal shape, upper petal: Broadly obovate. Petal shape, lateral and lower petals: Cordate. Petal apex, upper petal: Emarginate. Petal apex, lateral and lower petals: Obcordate. Petal margin, all petals: Entire. Petal texture, upper and lower surfaces, all petals: Smooth, glabrous. Color: All petals, when opening and fully opening, upper surface: 9A; lines towards the base, 166A. All petals, when opening and fully opening, lower surface: 9B. Throat: 1B. Tube: 1B.

*Calyx.*—Quantity per flower: Two sepals. Sepal length: About 6.9 mm. Sepal width: About 3.4 mm. Sepal shape: Linear. Sepal apex: Acute. Sepal base: Acute. Sepal margin: Entire. Sepal texture, upper and lower surfaces: Smooth, glabrous. Sepal color, upper and lower surfaces: 144A.

*Flower bracts.*—Arrangement: A single whorl of three bracts. Length: About 7.6 mm. Width: About 9.4 mm. Shape: Roughly elliptical. Apex: Acute. Margin: Entire. Texture, upper and lower surfaces: Smooth, glabrous. Color, upper and lower surfaces: 144A.

*Peduncles.*—Length: About 1.7 cm. Diameter: About 4 mm. Texture: Smooth, glabrous. Color: 144A.

*Reproductive organs.*—Stamens: Quantity per flower: Four. Anther shape: Ellipsoidal. Anther length: About 0.4 mm. Anther color: 155D. Pollen amount: Scarce. Pollen color: 155A. Pistils: Quantity per flower: One. Pistil length: About 7 mm. Style length: About 2 mm. Style color: 144A. Stigma shape: Ellipsoidal. Stigma color: 144C. Ovary color: 144A. Seed/fruit: Seed and fruit production has not been observed.

Disease/pest resistance: Plants of the new *Mecardonia* have not been shown to be resistant to pathogens and pests common to *Mecardonia*.

Temperature tolerance: Plants of the new *Mecardonia* have been observed to tolerate temperatures ranging from about 0° C. to about 35° C.

It is claimed:

1. A new and distinct *Mecardonia* plant named 'Sunmecareki' as illustrated and described.

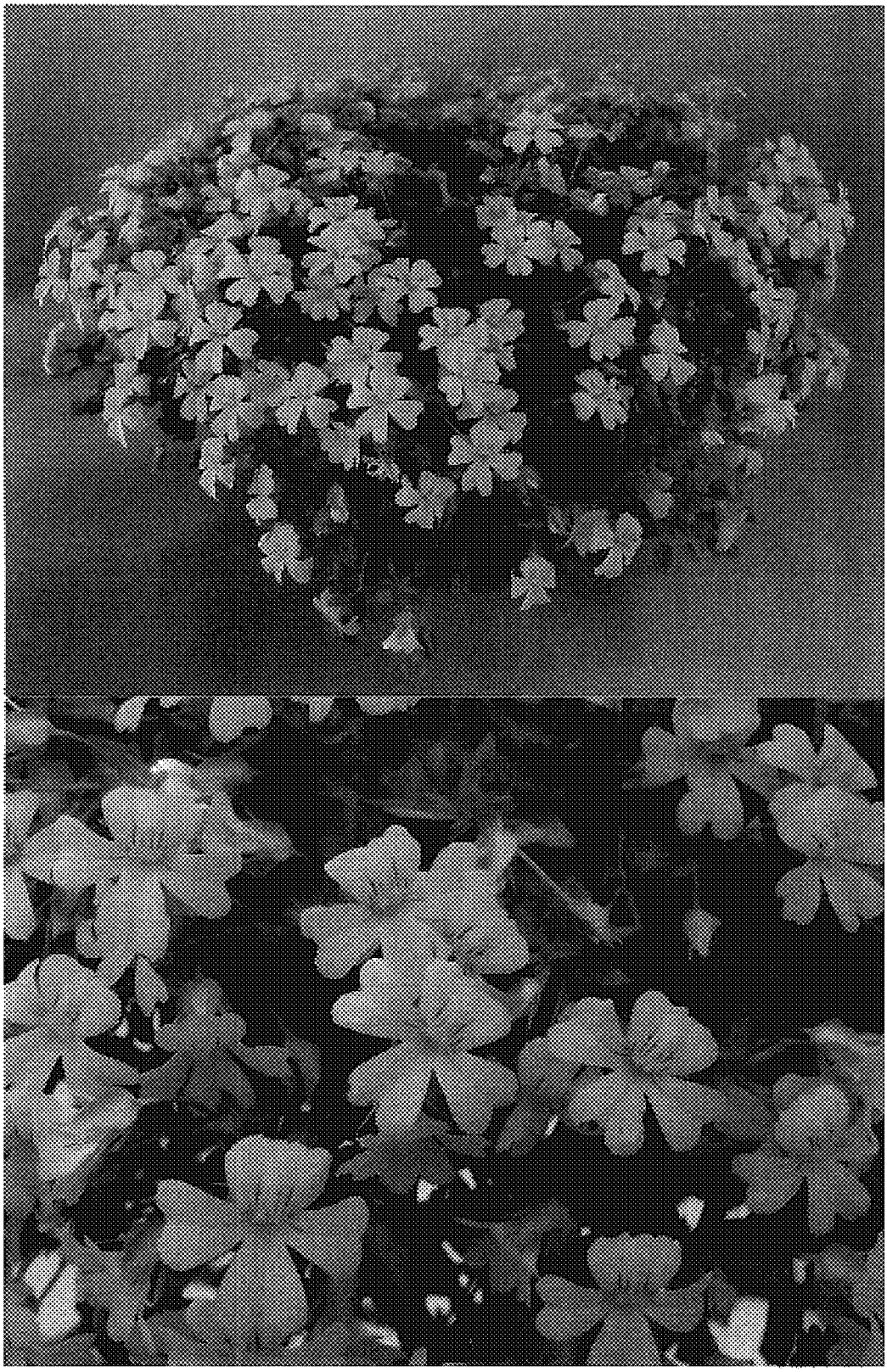

* * * * *